(12) United States Patent
Harris

(10) Patent No.: US 8,691,262 B2
(45) Date of Patent: Apr. 8, 2014

(54) METHOD FOR ALIGNING CELLS AND APPLYING HOMOGENOUS STRAIN THROUGHOUT DEFORMABLE ENGINEERED TISSUE CONSTRUCTS

(75) Inventor: Matthew Thomas Harris, New Haven, CT (US)

(73) Assignee: Matthew Thomas Harris, Tucson, AZ (US)

( * ) Notice: Subject to any disclaimer, the term of this patent is extended or adjusted under 35 U.S.C. 154(b) by 0 days.

(21) Appl. No.: 13/568,057

(22) Filed: Aug. 6, 2012

(65) Prior Publication Data

US 2013/0039985 A1    Feb. 14, 2013

Related U.S. Application Data

(60) Provisional application No. 61/521,409, filed on Aug. 9, 2011.

(51) Int. Cl.
*A61F 2/02* (2006.01)

(52) U.S. Cl.
USPC ........................................................ 424/423

(58) Field of Classification Search
CPC ........................ B32B 2318/00; B32B 2323/00
See application file for complete search history.

(56) References Cited

U.S. PATENT DOCUMENTS 6,998,265 B2 *    2/2006    Banes ........................... 435/401

* cited by examiner

*Primary Examiner* — Carlos Azpuru

(57) ABSTRACT

A process creates a homogenous sheet of engineered tissue comprised of encapsulated cells and a deformable engineered tissue construct. In the embodiment consisting of a collagen construct with encapsulated cells capable of contracting the matrix, the collagen fibers and encapsulated cells are aligned during the process. An apparatus can deliver controlled homogenous strain and stress to a thin sheet of engineered tissue. This process allows application of dynamic, uniform tensile loading to deformable engineered tissue constructs and creation of an engineered cell-delivery construct with alignment of both fibers and encapsulated cells.

19 Claims, 7 Drawing Sheets

METHOD FOR ALIGNING CELLS AND APPLYING HOMOGENOUS STRAIN THROUGHOUT DEFORMABLE ENGINEERED TISSUE CONSTRUCTS

BACKGROUND OF THE INVENTION

Tissue engineers attempt to generate biological constructs consisting of cells and delivery scaffolds in the laboratory; one goal is to create a biocompatible construct that may regenerate or augment healing of native living tissue. A variety of cell-types and many choices for delivery scaffold are available. Some cell types (pluripotent cells) may change their phenotype depending on the chemical and mechanical signals from their surrounding matrix. In the case of engineered tissue constructs that can recover from mechanical deformation, including constructs using a collagen matrix, the mechanical load on the matrix may alter pluripotent cell phenotype. Unfortunately, current methods of transmitting a tensile load to a deformable cell-delivery construct cause stress concentrations within the gel due to gripping effects. These stress concentrations cause non-homogenous mechanical signals to encapsulated cells, and fibers and cells within the deformable engineered tissue construct are not uniformly organized. Both of these effects are undesirable for some tissue engineering applications.

FIELD OF THE INVENTION

The invention pertains to the field of tissue engineering. More particularly, the invention pertains to cells encapsulated in a deformable matrix, i.e. deformable engineered tissue constructs.

DESCRIPTION OF RELATED ART

Numerous cell-delivery constructs are presently used including 1) hydrogels delivered by means of fluid injection, surgical suture or patch, 2) polymers of varying viscosity, permeability, and material strength and 3) ceramic compositions. Some polymers and most ceramics cannot recover from elastic deformation, and cells delivered with a brittle cell-delivery construct will not experience dynamic mechanical tensile loading. This lack of dynamic signal may negatively impact cell viability and maintenance of phenotype. Some thin sheets of deformable engineered tissue are constituted in absence of applied mechanical strain; encapsulated cells and surrounding matrix lacking controlled mechanical tension comprise a dynamic biological environment that results in deformable engineered tissue constructs with poor cell viability and poor matrix and construct mechanical integrity in comparison with thin sheets of deformable engineered tissue that are subjected to tension by control of interior geometry dimensions. Many manufactured polymers and hydrogels lack alignment of encapsulated cells and, or, matrix components including but not limited to protein fibers; some tissue healing applications would benefit from an engineered tissue with aligned fibers. Unfortunately, many state-of-the-art methods of introducing fiber alignment in hydrogels and other deformable cell-delivery constructs require mechanical gripping of the gel. This causes stress concentrations, nonhomogenous strain, and a non-uniform mechanical signal to the encapsulated cells. A related technology uses a flexible membrane that expands and stretches annularly on application of vacuum pressure from below the membrane, but this technology is limited because it requires anchoring the deformable engineered tissue construct to the flexible flat membrane and lacks homogenous strain throughout the deformable engineered tissue construct. The inventor claims that the method herein described is a significant improvement over the work of Banes et al, including U.S. Pat. No. 6,998,265 for the reasons stated in the following summary.

SUMMARY OF THE INVENTION

In one embodiment, the invention is a method for applying homogenous strain to deformable engineered tissue constructs for the purpose of manufacturing sheets, tubes, and strips of engineered tissue. By forming a deformable engineered tissue construct in a thin layer about an expandable body central to the construct, the construct will undergo uniform strain when the central body expands. The result of this process is the creation of an engineered construct consisting of a strained cell-delivery scaffold containing encapsulated cells that received uniform mechanical signals. This eliminates the problem of gripping effects in related art, and it also eliminates the need to anchor the deformable engineered tissue construct to a surface in order to transmit mechanical conditioning to the construct.

In another embodiment, a deformable engineered tissue construct comprised of collagen, alginate, agarose or other biocompatible or bioinert cell-delivery scaffold material is constituted in a thin layer surrounding an expandable central body. The hydrogel contains encapsulated cells including, but not limited to, schwann cells, fibroblasts, mesenchymal stem cells, smooth muscle cells, osteoblasts, tenocytes, keratinocytes and embryonic stem cells. By increasing the outer perimeter of the central expandable body, the encapsulated cells in the hydrogel will experience a uniform mechanical signal.

In another illustrative aspect, as a construct consisting of cells encapsulated in a cylindrical shell of collagen constituted about a central cylinder, the advantage over prior art is the creation of a construct with uniform fibrillar and cellular alignment and a homogenous population of cells that underwent uniform mechanical conditioning through their cell-matrix interactions. In this embodiment, due to the special property of collagen contraction by encapsulated cells possessing the required cell-matrix receptors, the cell-mediated contraction will cause alignment of the collagen fibrils and elongation and alignment of the encapsulated cells. By vertically compressing the cylinder, dynamic circumferential tensile strain may be applied to the surrounding deformable engineered tissue construct and encapsulated cells. By slicing the cylindrical shell of collagen vertically, a sheet of homogenous aligned collagen with aligned and elongated encapsulated cells that received uniform strain is obtained.

The products of these embodiments may be used to manufacture engineered tissue wound dressings, engineered surgical grafts, engineered tissue for delivering medicines and cell therapies, and as a means to control cell phenotype through mechanical signaling throughout the surrounding matrix within the deformable engineered tissue construct.

DETAILED DESCRIPTION OF THE INVENTION

Figure 1:
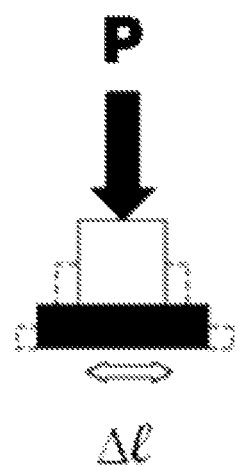
FIG. 1 shows, in profile, a vertical downward force "P" applied to a compressible cylinder (white) with a torus of deformable engineered tissue construct wrapped around the cylinder (black). Upon compression, the circumferential expansion "$\Delta l$" of the cylinder causes uniform tensile strain and elongation of the encircling torus of deformable engineered tissue construct (dashed lines).
Figure 2:
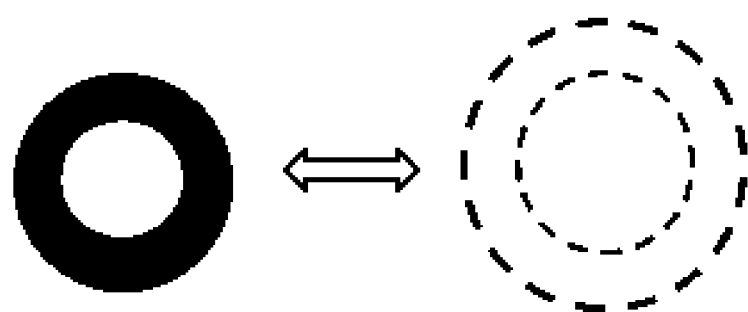
FIG. 2 shows an overhead view of the recoverable deformation described in FIG. 1. Expansion of the central cylinder causes uniform circumferential strain in the deformable engineered tissue construct (dashed).

In one embodiment, as shown in FIGS. 1 and 2, application of compression to a cylinder causes an increase in circumference. A continuous, deformable engineered tissue construct encircling the cylinder will undergo strain in proportion to the increase in cylinder circumference. Since the deformable engineered tissue construct is neither gripped nor anchored to a surface in order to cause the strain, there are no stress concentrations and the strain is homogenous. Application of strain to a deformable engineered tissue construct without gripping or anchoring effects and associated stress concentrations is an advantage of this invention over prior art.

Figure 3:
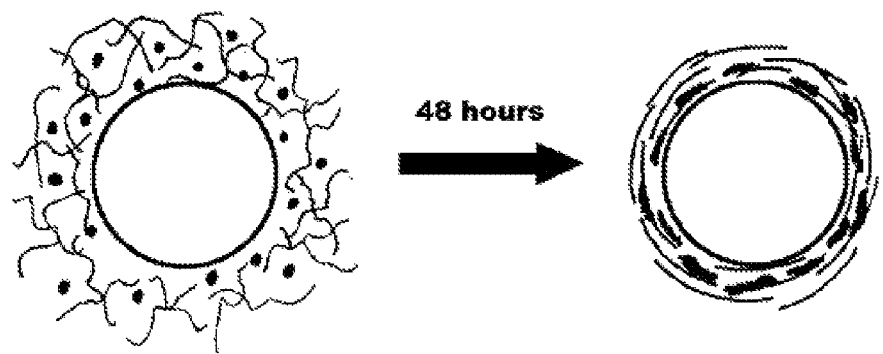
FIG. 3 shows encapsulated cells (black dots) and surrounding disorganized collagen fibers (wavy lines) initially poured about a central cylinder. After 48 hours of cell-mediated contraction, the collagen fibers are aligned, the encapsulated cells are elongated and aligned with the fibers, and the gel is contracted around the central cylinder.
Figure 4:
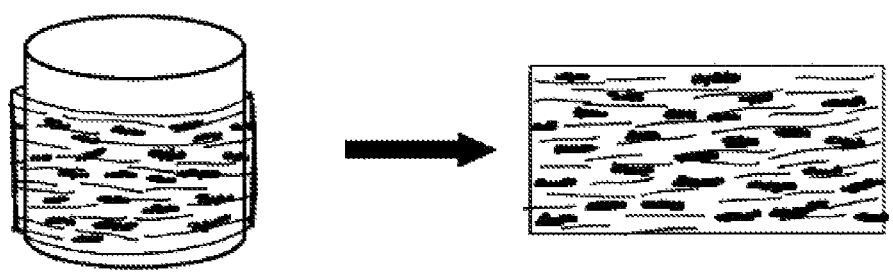
FIG. 4 shows contracted, aligned fibers of collagen (thin solid lines) and encapsulated cells (black ovals) in a cylindrical shell about a cylindrical post. By slicing the cylindrical shell of cells and collagen, a homogenous sheet of aligned collagen fibers and cells is obtained.
Figure 5:
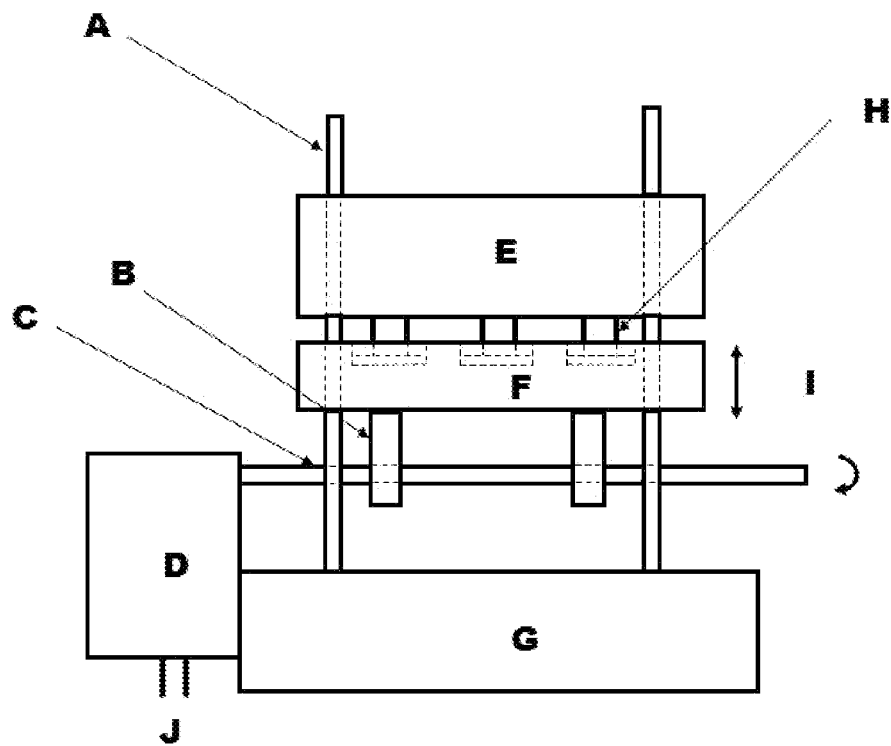
FIG. 5 shows an embodiment of an apparatus used to control the inner geometry of a thin sheet of deformable engineered tissue construct. "A" indicates vertical guide rods, "B" indicates an eccentric cam at 80% maximum vertical height with rotation driven by axle "C." "D" indicates a motor and motor housing used to rotate the axle to which eccentric cams are mounted. "E" indicates an overhead plate fixed in place to the vertical guide rods "A". "F" indicates a multi-well culture plate able to translate vertically along guide rod "A." "G" indicates a base for the apparatus. "H" indicates a deformable silicone post that undergoes vertical compression and circumferential expansion when the multi-well culture plate "F" is pushed upward towards the overhead fixed plate "E" by rotation of the eccentric cams "B" such that "H" undergoes vertical compression between "F" and "E." The arrows near "I" indicate direction of movement for the multi-well culture plate, "F", and the axle, "C", driving rotation of the eccentric cams. "J" indicates positive and negative leads on the motor housing allowing control of axle rotation by connecting a power source to the motor.
Figure 6:
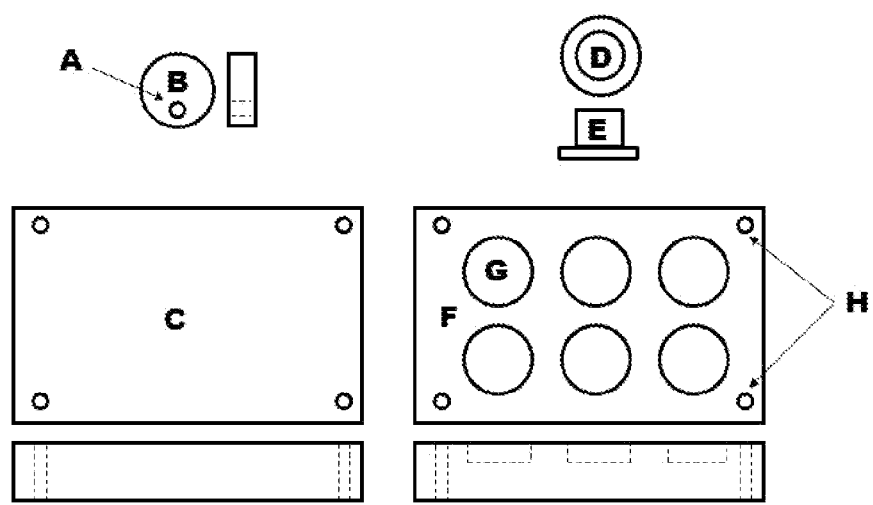
FIG. 6 shows a through hole, "A", in a front-view of an eccentric cam "B". "C" shows an overhead view of a fixed plate with four through holes for vertical guide rods, as shown in the assembly detailed in FIG. 5. "D" shows an overhead view of a deformable silicone post; "E" shows a profile view of the same deformable silicone post. "F" shows a multi-well movable culture plate with six wells, "G", used to hold deformable silicone posts "D", and four through holes, "H", allowing vertical translation along vertical guide rods as shown in the assembly of FIG. 5.
Figure 7:
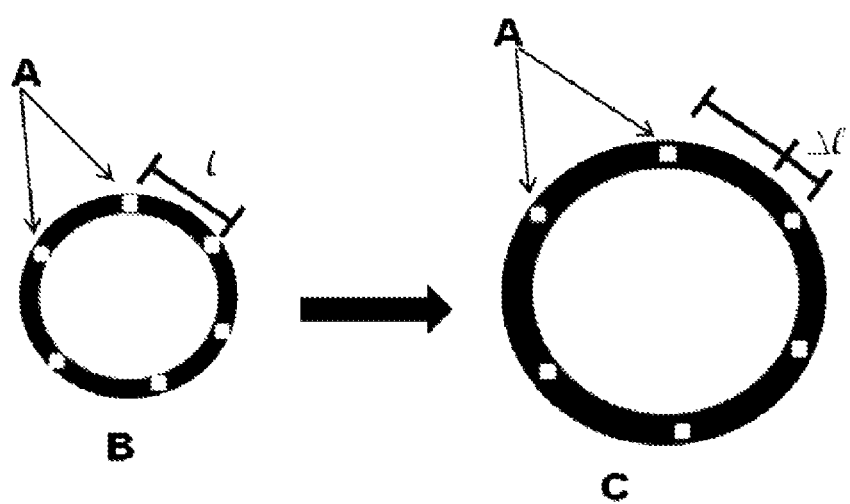
FIG. 7 shows the method used to quantify uniform strain throughout the deformable engineered construct. Lightweight opaque markers, white squares marked "A", were placed on the surface of an unstrained deformable torus of engineered tissue, black circle labeled "B", at regular intervals. An initial length between opaque markers was measured from a digital photograph, indicated by dimension "l." The deformable torus of engineered tissue underwent 5% circumferential strain leading to an elongated torus, indicated by black circle "C." The new distance between opaque surface markers was measured, with the increase labeled "Δl." Displacements were measured between each adjacent pair of opaque surface markers in the unstrained and strained condition to quantify uniform strain throughout the deformable engineered tissue construct.

In the embodiment shown in FIG. 3, a collagen hydrogel with encapsulated cells that cause cell-mediated contraction of the gel, the fibers of collagen and encapsulated cells undergo alignment around the central cylindrical post during the cell-mediated contraction process. In this embodiment, as shown in FIG. 4, by clipping the contracted gel of aligned fibers and cells, a strip or sheet of uniform engineered tissue results comprising: elongated cells, cellular and matrix alignment, and anisotropy, and construct homogeneity. This process eliminates gripping effects found in existing technology, and takes advantage of the cell-mediated collagen contraction to align the fibers. In this embodiment, encapsulated cells might include, but are not limited to schwann cells, mesenchymal stem cells, fibroblasts, osteoblasts, tenocytes, keratinocytes, embryonic stem cells and myocytes. This method of aligning collagen fibers and elongating and aligning encapsulated cells through cell-mediated contraction of matrix and uniform central geometrical constraint of the contraction phenomenon is an advantage over existing prior art that attempts to grip a deformable engineered tissue construct or anchor the construct to a flexible membrane.

In the embodiment shown in FIG. 4, an apparatus allows dynamic control of the interior geometry of a thin sheet, tube, or torus of deformed engineered tissue construct. This control of the interior geometry may be used for the purpose of creating a homogenous tensile pre-load throughout the deformable engineered tissue construct or dynamic mechanical conditioning of the deformable engineered tissue construct by cyclic, one-time (i.e. static), and varied duty-cycle application of homogenous strain and tension to the surrounding deformable engineered tissue construct. Homogenous strain may be applied using a wide variety of input waveforms in order to achieve varied mechanical milieus for the purpose of cell-conditioning. Application of homogenous static and dynamic mechanical load and strain throughout a deformable engineered tissue construct without gripping effects is an advantage of this invention over existing prior art.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

EXAMPLES

Example 1

3% Alginate Gel Formed in a Cylindrical Shell about a Central Silicone Cylinder A 3% alginate gel containing encapsulated cells was constituted around a deformable silicone cylinder. By vertically compressing the cylinder, the cylinder circumference increased by 5%. This 5% increase in circumference was translated to the surrounding alginate; reflective markers were embedded in the alginate and displacement was measured upon applying strain to the gel. The 6.8+/−3.2% (Mean+/−S.D.) strain measured using the embedded reflective markers of corroborated the theoretical 5% strain within the alginate upon compression of the silicone cylinder. The data also supported a uniform strain distribution.

Example 2

4 mg/mL Type-I Collagen Gel Formed in a Cylindrical Shell about a Central Silicone Cylinder A 4 mg/mL type-I collagen gel from rat tail tendon was formed in a torus about a deformable silicone cylinder. By vertically compressing the cylinder, a 5% increase in the cylinder circumference results. This 5% increase in circumference was translated to the surrounding type-I collagen; reflective markers were embedded in the collagen and displacement was measured upon applying strain to the gel. The 8.1+/−2.9% (Mean+/−S.D.) strain measured using the embedded reflective markers corroborated the theoretical 5% strain within the collagen upon compression of the silicone cylinder. The data also supported a uniform strain distribution.

Example 3

1 Million Human Mesenchymal Stem Cells per ml in 4 mg/ml Type I Collagen Gel Human mesenchymal stem cells at passage 8 were mixed with 4 mg/ml type I collagen gel from rat tail tendon. After 48 hours, a live/dead assay consisting of calcein and ethidium homodimer stained encapsulated cells. Collagen fibrils were imaged using the method of second harmonic excitation. Cells and fibrils showed qualitative alignment under confocal microscopy.

Example 4

160 k Human Mesenchymal Stem Cells per ml of 4 mg/ml Type I Collagen Gel: Strain Response Human mesenchymal stem cells at passage 6 were mixed with 4 mg/ml type I collagen gel from rat tail tendon at a density of 160 k cells/ml. These cell-seeded collagen gels were poured in a torus of volume 750 microliters around a cylindrical silicone post of diameter 0.4". These torus-shaped gels were cultured for 3 weeks, and the strain transmitted through the gel was quantified by placing reflective markers on top of the gel and measuring strain within the gel after applying a 5% circumferential strain to the central post. Strain was measured using ImageJ software (NIH, Bethesda, Md.) by calculating the linear displacement between markers before and after 5% applied strain. Although some variability in strain was present, the gels retained ability to recover from and transmit strain over three weeks of culture.

Example 5

$5 \times 10^5$ Human MSCs/ml Type-I Collagen Gel Deformable Engineered Tissue Constructs Recover from 5% Strain for 3 Weeks and Display Cellular Elongation and Anisotropy after Seven Days of Culture Using a Torus Thin Sheet Geometry A custom in-house bioreactor was manufactured to apply strain to cell-seeded collagen gels. Cams fixed to an axle drive a moving plate vertically into a fixed plate. This compresses a deformable silicone post and strains the encircling collagen torus. Human mesenchymal stem cells (hMSCs) (Lonza PT-2501) were cultured and encapsulated in Type I collagen gel. $5 \times 105$ hMSC/ml gels were cultured as "unconstrained" gels and torus-shaped gels cultured under either static or dynamic strain. The "unconstrained" control group gels were cultured inside standard 12-well plates. The dynamic strain group received 5% strain by increasing the silicone post circumference for 50 cycles daily at 3 revolutions per minute (rpm). To investigate the effect of mechanical loading on cell morphology inside the 3D collagen matrix, cells were incubated with Live/Dead assay (Molecular Probes) and imaged with a confocal microscope. The quantification of the alignment was done through measuring the orientation of the major axis of the cell with respect to the horizontal; elongated cells were modeled as ellipses with major and minor axes. 10 cells were measured per image with ImageJ software (NIH). The Rayleigh test was used to check for random orientation. In order to understand the effect of mechanical loading on deformation of torus-shaped cell-seeded gels, local gel displacements were measured by applying surface markers at even intervals and quantifying displacement between markers before and after applying 5% strain to the inner circumference of the gel. This was repeated over three weeks, and results were compared between each group with an ANOVA and Tukey's test with $\alpha=0.05$. Unconstrained, freely contracting hMSC-seeded collagen gels were compared to collagen gels created in a torus around a post. Torus gels underwent either static culture or a dynamic strain protocol that increased the inner circumference by 5%. All gels poured as a torus exhibited qualitative cellular elongation and cellular anisotropy indicated by the Rayleigh test with a standard deviation of 28 degrees and 12 degrees from the mean angle of orientation for static and dynamically stretched torus gels, respectively. Cellular orientation appeared random for unconstrained gels on day seven with a standard deviation of 70 degrees from the mean orientation angle indicating lack of anisotropy by the Rayleigh test; i.e. the widest distribution of orientation angles occurred for unconstrained gels. When local gel strain was quantified using surface marker displacement, torus gels receiving daily dynamic strain maintained their response to applied strain for three weeks of culture, showing that application of strain at 5% magnitude was an elastic deformation for this specific deformable engineered tissue construct. Creation of an hMSC-seeded collagen gel in a torus around a post caused alignment of cells by seven days of culture. By preparing the gel in a torus and taking advantage of the cell-mediated contraction of collagen, this process yields a homogenous 3D construct. Furthermore, dynamic strain improved the alignment of cells in comparison with static culture. By using a torus of gel, strain can be applied to the gel without gripping effects. Experimental quantification of strain throughout the gel is important; the measurements illustrate whether the gel has failed or has a thin region. Furthermore, since the system aims to provide similar mechanical signals to cells throughout the gel, quantification of local strain corroborates that the input signal from the expansion of the interior geometry is passed to the thin sheet of surrounding deformable engineered tissue.

PARENT CASE TEXT

This application claims the benefit of provisional application No. 61/521,409 filed Aug. 9, 2011.

REFERENCES CITED

| U.S. Patent Documents | | |
|---|---|---|
| 4839280 | June 1989 | Banes |
| 4851354 | July 1989 | Winston et al. |
| 5153136 | October 1992 | Vandenburgh |
| 5348879 | September 1994 | Shapiro et al. |
| 5518909 | May 1996 | Banes |
| 5686303 | November 1997 | Korman |
| 6037141 | March 2000 | Banes |
| 6048723 | April 2000 | Banes |
| 6207451 | March 2001 | Dennis et al. |
| 6218178 | April 2001 | Banes |
| 6998265 | February 2006 | Banes |

The embodiments of the invention in which an exclusive property or privilege is claimed are defined as follows:

1. A method for mechanically conditioning a deformable engineered tissue construct comprising a continuous, closed deformable engineered tissue construct with a central opening constituted and wrapped around an expandable/collapsible inner geometry leading to a deformable engineered tissue construct that has undergone homogenous tensile mechanical conditioning without gripping effect.

2. The method defined in claim 1, wherein the closed deformable engineered tissue construct is constituted in the shape of a torus fashioned about a cylindrical inner geometry, whereby the closed deformable engineered tissue construct may be converted to a strip or sheet of homogenous deformable engineered tissue construct.

3. The method defined in claim 1, wherein the closed deformable engineered tissue construct consists of encapsulated cells possessing the means to biochemically interact with the surrounding matrix such that macroscopic static and dynamic tensile strain applied to the matrix of the closed deformable engineered tissue construct is transmitted to the encapsulated cells.

4. The method defined in claim 3, wherein the matrix surrounding the encapsulated cells is comprised of fibers of collagen or other lengthy polymer or protein able to mechanically interact with encapsulated cells leading to anisotropic, aligned matrix due to cellular reorganization of matrix during initial constitution of the closed deformable engineered tissue construct.

5. The method defined in claim 3, wherein the encapsulated cells undergo elongation and alignment with the surrounding matrix during the initial constitution of the closed deformable engineered tissue construct.

6. The method defined in claim 1, comprising the further step of:
adding a static, homogenous, tensile pre-load causing additional matrix and cellular alignment and anisotropy subsequent to the initial constitution of the closed deformable engineered tissue construct.

7. The method defined in claim 1, comprising the further step of:
adding a dynamic, homogenous, tensile mechanical load causing additional matrix and cellular alignment and anisotropy subsequent to the initial constitution of the closed deformable engineered tissue construct.

8. The method defined in claim 1, further including the step of applying a dynamic, homogenous, tensile strain signal throughout the closed deformable engineered tissue construct for the purpose of conditioning encapsulated cells and matrix throughout the continuous, deformable engineered tissue construct.

9. The method defined in claim 1, wherein the inner geometry consists of an expandable/collapsible sphere.

10. The method defined in claim 1, further including the step of applying a static, homogenous, tensile pre-load to the closed deformable engineered construct by expanding the inner geometry.

11. The method defined in claim 1, further including the step of applying a dynamic, homogenous, tensile strain throughout the closed deformable engineered tissue construct by expanding and contracting the inner geometry.

12. A method of mechanically conditioning a deformable tissue construct for use in augmenting healing of living tissue comprising the steps of:
forming the deformable tissue construct into a closed endless deformable tissue construct having a central opening;
placing the closed endless deformable tissue construct completely around an expandable body, wherein the expandable body is contained within the central opening;
expanding the expandable body applying a strain uniformly to the closed endless deformable tissue construct; and
removing the closed endless deformable tissue construct from the expandable body,
whereby the closed endless deformable tissue construct is subjected to a uniform strain without gripping effect.

13. A method of mechanically conditioning a deformable tissue as in claim 12 comprising the further step of:
using the closed endless deformable tissue construct in repairing living tissue.

14. A method of mechanically conditioning a deformable tissue as in claim 12 wherein:
the expandable body comprises a cylinder; and
the closed endless deformable tissue construct comprises a torus.

15. A method of mechanically conditioning a deformable tissue as in claim 12 wherein:
the closed endless deformable tissue construct comprises encapsulated cells and collagen fibers.

16. A method of mechanically conditioning a deformable tissue as in claim 15 comprising the further step of:
cyclically expanding the expandable body.

17. A method of mechanically conditioning a deformable tissue as in claim 12 wherein:

the closed endless deformable tissue construct comprises a cell delivery scaffold and encapsulated cells.

18. A method of mechanically conditioning a deformable tissue as in claim 12 wherein:

the expandable body comprises a sphere.

19. A method of mechanically conditioning a deformable tissue construct without gripping effect for use in augmenting healing of living tissue comprising the steps of:

forming the deformable tissue construct into a tubular deformable tissue construct having a central opening;

placing an expandable body within the central opening of the tubular deformable tissue construct, wherein the tubular deformable tissue construct surrounds the expandable body, expanding the expandable body within the central opening of the tubular deformable tissue construct applying a strain uniformly to the tubular deformable tissue construct; and removing the tubular deformable tissue construct from the expandable body, whereby the tubular tissue construct is subjected to a uniform strain without gripping effect.

* * * * *